US012733810B2

(12) United States Patent
Duffin et al.

(10) Patent No.: US 12,733,810 B2
(45) Date of Patent: Sep. 15, 2026

(54) DYNAMIC SUSCEPTIBILITY CONTRAST USING A PRE-DETERMINED ARTERIAL INPUT FUNCTION

(71) Applicant: THORNHILL SCIENTIFIC INC., North York (CA)

(72) Inventors: James Duffin, Toronto (CA); Joseph Arnold Fisher, Thornhill (CA); David Mikulis, Oakville (CA); Ece Su Sayin, Windsor (CA); Jacob B. Schulman, Toronto (CA); Olivia Sobczyk, Etobicoke (CA); Kamil Uludag, Toronto (CA)

(73) Assignee: THORNHILL SCIENTIFIC INC., North York (CA)

( * ) Notice: Subject to any disclaimer, the term of this patent is extended or adjusted under 35 U.S.C. 154(b) by 60 days.

(21) Appl. No.: 18/841,113

(22) PCT Filed: Feb. 27, 2023

(86) PCT No.: PCT/IB2023/051818
§ 371 (c)(1),
(2) Date: Aug. 23, 2024

(87) PCT Pub. No.: WO2023/161901
PCT Pub. Date: Aug. 31, 2023

(65) Prior Publication Data

US 2025/0160645 A1 May 22, 2025

Related U.S. Application Data

(60) Provisional application No. 63/313,996, filed on Feb. 25, 2022.

(51) Int. Cl.
*A61B 5/00* (2006.01)
*A61B 5/026* (2006.01)
(Continued)

(52) U.S. Cl.
CPC .......... *A61B 5/0036* (2018.08); *A61B 5/0263* (2013.01); *A61B 5/0275* (2013.01);
(Continued)

(58) Field of Classification Search
CPC ... A61B 5/0036; A61B 5/0263; A61B 5/0275; A61B 5/055; G01R 33/5601; G01R 33/56366
See application file for complete search history.

(56) References Cited

U.S. PATENT DOCUMENTS

2009/0120435 A1* 5/2009 Slessarev .............. A61M 16/12
128/203.14
2012/0220858 A1 8/2012 Carroll et al.
(Continued)

FOREIGN PATENT DOCUMENTS

WO WO-2012078823 A2 6/2012
WO WO-2021137196 A1 7/2021

OTHER PUBLICATIONS

Abels, Benjamin, et al. "Perfusion CT in acute ischemic stroke: a qualitative and quantitative comparison of deconvolution and maximum slope approach." American Journal of Neuroradiology 31.9 (2010): 1690-1698.

(Continued)

*Primary Examiner* — Joel F Brutus
(74) *Attorney, Agent, or Firm* — PERRY + CURRIER INC.

(57) ABSTRACT

Hypoxia-induced deoxyhemoglobin concentration ([dOHb]) may be used as a susceptibility contrast agent in subjects. With sequential gas delivery methods, reoxygenation can be implemented abruptly, inducing an arterial input function with a square shape. Since the concentration of deoxyhemoglobin is known, the arterial input function can be pre-determined and perfusion metrics can be completed
(Continued)

without error-prone measurements. Pre-determined arterial input functions provide a faster, more reliable method of analyzing BOLD-MRI images, and the resolution is not limited by the breath rate.

21 Claims, 4 Drawing Sheets

(51) Int. Cl.
*A61B 5/0275* (2006.01)
*A61B 5/055* (2006.01)
*G01R 33/56* (2006.01)
*G01R 33/563* (2006.01)

(52) U.S. Cl.
CPC .......... *A61B 5/055* (2013.01); *G01R 33/5601* (2013.01); *G01R 33/56366* (2013.01); *A61B 2576/00* (2013.01)

(56) References Cited

U.S. PATENT DOCUMENTS

| | | | | |
|---|---|---|---|---|
| 2014/0311491 | A1* | 10/2014 | Klein | A61M 16/0003 128/204.22 |
| 2016/0000935 | A1 | 1/2016 | Jiang et al. | |
| 2016/0220115 | A1 | 8/2016 | Fisher et al. | |
| 2017/0325784 | A1* | 11/2017 | Friedrich | A61B 8/5284 |
| 2020/0297960 | A1 | 9/2020 | O'Donnell et al. | |

OTHER PUBLICATIONS

Asaduddin, Muhammad, et al. "Mapping cerebral perfusion from time-resolved contrast-enhanced MR angiographic data." Magnetic resonance imaging 61 (2019): 143-148.
Ashburner, John et al., "Multimodal image coregistration and partitioning—a unified framework." Neuroimage 6.3 (1997): 209-217.
Bhogal, Alex A., et al. "Quantifying cerebral blood arrival times using hypoxia-mediated arterial BOLD contrast." NeuroImage 261 (2022): 119523.
Bleeker, Egbert JW, et al. "Evaluation of signal formation in local arterial input function measurements of dynamic susceptibility contrast MRI." Magnetic resonance in medicine 67.5 (2012): 1324-1331.
Blockley, Nicholas P., et al. "Sources of systematic error in calibrated BOLD based mapping of baseline oxygen extraction fraction." NeuroImage 122 (2015): 105-113.
Calamante, Fernando. "Perfusion MRI using dynamic-susceptibility contrast MRI: quantification issues in patient studies." Topics in magnetic resonance imaging 21.2 (2010): 75-85.
Chappell, Michael A. et al., "Correcting for large vessel contamination in dynamic susceptibility contrast perfusion MRI by extension to a physiological model of the vasculature." Magnetic resonance in medicine 74.1 (2015): 280-290.
Chen, Chushuang, et al. "Thresholds for infarction vary between gray matter and white matter in acute ischemic stroke: a CT perfusion study." Journal of Cerebral Blood Flow & Metabolism 39.3 (2019): 536-546.
Christiansen, Lasse, et al. "Acute intermittent hypoxia enhances corticospinal synaptic plasticity in humans." Elife 7 (2018): e34304.
Cologner, Julie, et al. "Transient hypoxia model revealed cerebrovascular impairment in anemia using BOLD MRI and near-infrared spectroscopy." Journal of magnetic resonance imaging 52.5 (2020): 1400-1412.
Conturo, Thomas E., et al. "Arterial input functions for dynamic susceptibility contrast MRI: requirements and signal options." Journal of Magnetic Resonance Imaging: An Official Journal of the International Society for Magnetic Resonance in Medicine 22.6 (2005): 697-703.
Cox, Robert W. "AFNI: Software for Analysis and Visualization of Functional Magnetic Resonance Neuroimages." Computers and Biomedical Research 29 (1996): 162-173.
Deacon, Naomi L., et al. "Intermittent hypercapnic hypoxia during sleep does not induce ventilatory long-term facilitation in healthy males." J Appl Physiol 123 (2017): 534-543.
Donahue, Manus J., et al. "Consensus statement on current and emerging methods for the diagnosis and evaluation of cerebrovascular disease." Journal of Cerebral Blood Flow & Metabolism 38.9 (2018): 1391-1417.
Donahue, Manus J., et al. "Bolus arrival time and cerebral blood flow responses to hypercarbia." Journal of Cerebral Blood Flow & Metabolism 34.7 (2014): 1243-1252.
Fierstra, Jorn, et al. "End-inspiratory rebreathing reduces the end-tidal to arterial PCO2 gradient in mechanically ventilated pigs." Intensive care medicine 37.9 (2011): 1543-1550.
Fisher, Joseph A. et al., "Sequential gas delivery provides precise control of alveolar gas exchange." Respiratory Physiology & Neurobiology 225 (2016): 60-69.
Fitzgerald, Bradley, et al. "Using carpet plots to analyze transit times of low frequency oscillations in resting state fMRI." Scientific reports 11.1 (2021): 7011.
Grandin, Cécile B., et al. "Absolute CBF and CBV measurements by MRI bolus tracking before and after acetazolamide challenge: repeatabilily and comparison with PET in humans." Neuroimage 26.2 (2005): 525-535.
Helenius, J., et al. "Cerebral Hemodynamics in a Healthy Population Measured by Dynamic Susceptibility Contrast MR Imaging." Acta Radiologica 44 (2003): 538-546.
Hoge, Richard D., et al. "Investigation of BOLD signal dependence on cerebral blood flow and oxygen consumption: the deoxyhemoglobin dilution model." Magnetic resonance in medicine: An official journal of the international society for magnetic resonance in medicine 42.5 (1999): 849-863.
Ibaraki, Masanobu, et al. "Cerebral vascular mean transit time in healthy humans: a comparative study with PET and dynamic susceptibility contrast-enhanced MRI." Journal of Cerebral Blood Flow & Metabolism 2007.27 (2006): 404-413.
Lee, DongKyu, et al. "Whole-brain perfusion mapping in mice by dynamic BOLD MRI with transient hypoxia." Journal of Cerebral Blood Flow & Metabolism 42.12 (2022): 2270-2286.
Madsen, M. T. "A simplified formulation of the gamma variate function." Physics in Medicine and Biology 37.7 (1992): 1597-1600.
Mardimae, Alexandra, et al. "The interaction of carbon dioxide and hypoxia in the control of cerebral blood flow." Pflügers Archiv—European Journal of Physiology 464.4 (2012): 345-351.
Mark, Clarisse I. et al., "Metabolic and vascular origins of the BOLD effect: Implications for imaging pathology and resting-state brain function." Journal of Magnetic Resonance Imaging 42.2 (2015): 231-246.
McGehee, Blake E. et al., "Brain Perfusion Imaging: How Does It Work and What Should I Use?." Journal of Magnetic Resonance Imaging 36 (2012): 1257-1272.
Mouridsen, Kim, et al. "Bayesian estimation of cerebral perfusion using a physiological model of microvasculature." Neuroimage 33.2 (2006): 570-579.
Newbould, Rexford D., et al. "Perfusion mapping with multiecho multishot parallel imaging EPI." Magnetic Resonance in Medicine: An Official Journal of the International Society for Magnetic Resonance in Medicine 58.1 (2007): 70-81.
Ogawa, Seiji, et al. "Brain magnetic resonance imaging with contrast dependent on blood oxygenation." proceedings of the National Academy of Sciences 87.24 (1990): 9868-9872.
Paling, David, et al. "Cerebral arterial bolus arrival time is prolonged in multiple sclerosis and associated with disability." Journal of Cerebral Blood Flow & Metabolism 34.1 (2014): 34-42.
Poublanc, Julien, et al. "Perfusion MRI using endogenous deoxyhemoglobin as a contrast agent: Preliminary data." Magnetic resonance in medicine 86.6 (2021): 3012-3021.
Uludag, Kâmil et al., "Linking brain vascular physiology to hemodynamic response in ultra-high field MRI." Neuroimage 168 (2018): 279-295.

(56) References Cited

OTHER PUBLICATIONS

Poulin, M. J. et al., "Dynamics of the cerebral blood flow response to step changes in end-tidal PCO2 and PO2 in humans." Journal of applied physiology 81.3 (1996): 1084-1095.

Sebok, Martina, et al. "Mapping Cerebrovascular Reactivity Impairment in Patients With Symptomatic Unilateral Carotid Artery Disease." (2021).

Shiroishi, Mark S., et al. "Principles of T2*-weighted dynamic susceptibility contrast MRI technique in brain tumor imaging." Journal of magnetic resonance imaging 41.2 (2015): 296-313.

Slessarev, Marat, et al. "Prospective targeting and control of end-tidal CO2 and O2 concentrations." J Physiol 581 (2007): 1207-1219.

Sobczyk, Olivia, et al. "Assessing cerebrovascular reactivity abnormality by comparison to a reference atlas." Journal of Cerebral Blood Flow & Metabolism 35.2 (2015): 213-220.

Sobczyk Olivia, et al. "The reproducibility of cerebrovascular reactivity across MRI scanners." Frontiers in physiology 12 (2021): 668662.

Tsujikawa, Tetsuya, et al. "Arterial transit time mapping obtained by pulsed continuous 3D ASL imaging with multiple post-label delay acquisitions: comparative study with PET-CBF in patients with chronic occlusive cerebrovascular disease." PLoS One 11.6 (2016): e0156005.

Uludag, Kâmil et al., "An integrative model for neuronal activity-induced signal changes for gradient and spin echo functional imaging." NeuroImage 48 (2009): 150-165.

Vu, Chau, et al. "Quantitative perfusion mapping with induced transient hypoxia using BOLD MRI." Magnetic resonance in medicine 85.1 (2021): 168-181.

Watabe, Tadashi, et al. "CBF/CBV maps in normal volunteers studied with 15O PET: a possible index of cerebral perfusion pressure." Neurosci Bull 30.5 (2014): 857-862.

Wirestam, Ronnie, et al. "Comparison of quantitative dynamic susceptibility-contrast MRI perfusion estimates obtained using different contrast-agent administration schemes at 3 T." European journal of radiology 75.1 (2010) : e86-e91.

Yao, Jinxia Fiona et al., "Cerebral Circulation Time Derived From fMRI Signals in Large Blood Vessels." J Magn Reson Imaging 50.5 (2019): 1504-1513.

Yao, Jinxia, et al. "A novel method of quantifying hemodynamic delays to improve hemodynamic response, and CVR estimates in CO2 challenge fMRI." Journal of Cerebral Blood Flow & Metabolism 41.8 (2021): 1886-1898.

Calamante, Fernando. "Arterial input function in perfusion MRI: a comprehensive review." Progress in nuclear magnetic resonance spectroscopy 74 (2013): 1-32.

Balaban, Dahlia Y., et al. "The in-vivo oxyhaemoglobin dissociation curve at sea level and high altitude." Respiratory physiology & neurobiology 186.1 (2013): 45-52.

Ito, Shoji, et al. "Non-invasive prospective targeting of arterial P in subjects at rest." The Journal of physiology 586.15 (2008): 3675-3682.

* cited by examiner

DYNAMIC SUSCEPTIBILITY CONTRAST USING A PRE-DETERMINED ARTERIAL INPUT FUNCTION

CROSS-REFERENCE TO RELATED APPLICATION(S)

This application claims the benefit of U.S. provisional application entitled "The use of the end-tidal $PO_2$ ($P_{ET}O_2$) as the AIF" having Ser. No. 63/313,996, filed Feb. 25, 2022 and incorporated in its entirety by reference herein.

FIELD

The present specification is directed to perfusion MRI, and specifically methods and systems for using deoxyhemoglobin as a contrast agent.

BACKGROUND

Many common conditions such as cigarette smoking, high blood cholesterol, obesity, sedentary lifestyle, diabetes, hypertension, and aging result in silently accumulating cerebrovascular pathologies, for example small vessel disease, venous collagenases, chronic inflammation and multiple subcortical infarcts. The health of cerebral perfusion can be assessed by perfusion metrics calculated using dynamic susceptibility contrast (DSC).

A considerable source of error in the calculation of perfusion metrics is the uncertainty of the arterial input function (AIF). To determine the AIF, a magnetic resonance imaging (MRI) signal is typically measured over a large artery such as the middle cerebral artery (MCA) while implementing a bolus of contrast agent. Unfortunately, this method of determining the AIF is not practical when the MCA is small, or oriented in a direction not suitable to measure the AIF, or in organs that lack sufficiently large arteries, for example, the thyroid gland. Failing that, no AIF can be identified, precluding calculation of hemodynamic metrics. Furthermore, with respect to calculating deoxyhemoglobin from end-tidal breath values as a contrast agent, the temporal resolution for the AIF is limited to the respiratory rate, which may be significantly longer than the TR of the MRI system.

SUMMARY

It is one aspect of the disclosure to provide a method of determining a perfusion metric in a subject. The method includes pre-determining an arterial input function by selecting a square input function that corresponds to a first end tidal partial pressure of oxygen ($P_{ET}O_2$), a second $P_{ET}O_2$, and an end tidal partial pressure of carbon dioxide ($P_{ET}CO_2$). The method further includes inducing an increase in arterial partial pressure of oxygen in a subject by targeting the first $P_{ET}O_2$ with a sequential gas delivery device and targeting the second $P_{ET}O_2$ with the sequential gas delivery device while controlling $P_{ET}CO_2$. The first $P_{ET}O_2$ is less than the second $P_{ET}O_2$. The method further includes measuring a magnetic signal in a selected voxel in the subject responsive to the increase in arterial partial pressure of oxygen. The method further includes outputting a perfusion metric for the selected voxel at a display. The perfusion metric is computed based on the pre-determined arterial input function and the magnetic signal.

Optionally, the sequential gas delivery device is configured to induce the increase in arterial partial pressure of oxygen abruptly, and in some examples, within one breath.

Optionally, the first $P_{ET}O_2$ corresponds to hypoxia in the subject and the second $P_{ET}O_2$ corresponds to normoxia in the subject.

Optionally, the first $P_{ET}O_2$ is about 40 mmHg and the second $P_{ET}O_2$ is about 95 mmHg.

Optionally, controlling the $P_{ET}CO_2$ maintaining normocapnia while targeting the first and second $P_{ET}O_2$.

Optionally, the perfusion metric is cerebral blood flow, mean transit time, or cerebral blood volume.

Optionally, the magnetic signal is measured using blood oxygen level dependent magnetic resonance imaging.

It is another aspect of the disclosure to provide a system for determining a perfusion metric in a subject. The system includes a processor, a sequential gas delivery device, an imaging device, and a display. The processor is configured to pre-determine an arterial input function. The arterial input function is a square input function that corresponds to a first $P_{ET}O_2$, a second $P_{ET}O_2$, and an end tidal partial pressure of carbon dioxide ($P_{ET}CO_2$). The sequential gas delivery device is configured to induce an increase in arterial partial pressure of oxygen in a subject by targeting the first $P_{ET}O_2$ and targeting the second $P_{ET}O_2$, while controlling the $P_{ET}CO_2$. The first $P_{ET}O_2$ is less than the first $P_{ET}O_2$. The imaging device is configured to measure a magnetic signal in a selected voxel in the subject responsive to the increase in arterial partial pressure of oxygen. The display is configured to output a perfusion metric calculated for the selected voxel, the perfusion metric computed based on the pre-determined arterial input function and the magnetic signal.

Optionally, the sequential gas delivery device is configured to induce the increase in arterial partial pressure of oxygen abruptly, and in some examples, within one breath.

Optionally, the first $P_{ET}O_2$ is selected to induce hypoxia in the subject and the second $P_{ET}O_2$ is selected to induce normoxia in the subject.

Optionally, the first $P_{ET}O_2$ is about 40 mmHg and the second $P_{ET}O_2$ is about 95 mmHg.

Optionally, the sequential as delivery device is further configured to maintain normocapnia while targeting the first and second $P_{ET}O_2$.

Optionally, the perfusion metric is cerebral blood flow, mean transit time, or cerebral blood volume.

Optionally, the imaging device is configured to measure the magnetic signal using blood oxygen level dependent magnetic resonance imaging.

It is yet a further aspect of the disclosure to provide a non-transitory computer-readable medium comprising instructions for determining a perfusion metric in a subject.

The instructions include pre-determining an arterial input function. The arterial input function is a square input function corresponding to a first $P_{ET}O_2$, a second $P_{ET}O_2$, and a $P_{ET}CO_2$. The instructions further include controlling a sequential gas delivery device to induce an increase in arterial partial pressure of oxygen in a subject by targeting the first $P_{ET}O_2$ and targeting the second $P_{ET}O_2$ while controlling the $P_{ET}CO_2$. The first $P_{ET}O_2$ is less than the second $P_{ET}O_2$. The instructions further include measuring a magnetic signal in a selected voxel in the subject responsive to the increase in arterial partial pressure of oxygen. The instructions further include outputting a perfusion metric for the selected voxel at a display, the perfusion metric computed based on the pre-determined arterial input function and the magnetic signal.

Optionally, the instructions include controlling the sequential gas delivery device to induce the increase in arterial partial pressure of oxygen abruptly. In some examples, the sequential gas delivery device is controlled to induce the increase within one breath.

Optionally, the first $P_{ET}O_2$ corresponds to hypoxia in the subject and the second $P_{ET}O_2$ corresponds to normoxia in the subject.

Optionally, the first $P_{ET}O_2$ is about 40 mmHg and the second $P_{ET}O_2$ is about 95 mmHg.

Optionally, the instructions further include controlling the sequential gas delivery device to maintain normocapnia while targeting the first and second $P_{ET}O_2$.

Optionally, the perfusion metric is cerebral blood flow, mean transit time, or cerebral blood volume.

Optionally, the magnetic signal is measured using blood oxygen level dependent magnetic resonance imaging.

These together with other aspects and advantages which will be subsequently apparent, reside in the details of construction and operation as more fully hereinafter described and claimed, reference being had to the accompanying drawings forming a part hereof, wherein like numerals refer to like parts throughout.

BRIEF DESCRIPTION OF THE DRAWINGS

The present disclosure will be described with respect to the following figures.

DETAILED DESCRIPTION

Figure 1:
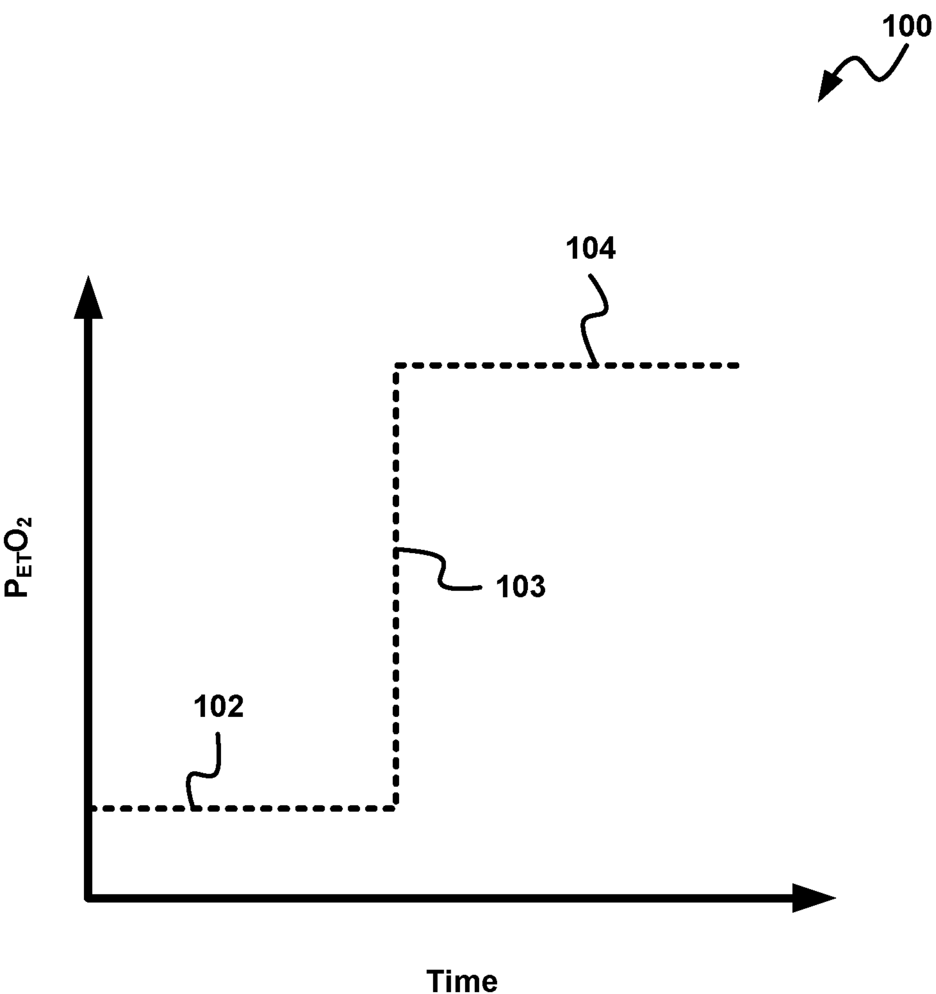
FIG. 1 is a diagram representing the surface area of a lung.

"AIF" herein refers to arterial input function, which is the concentration of a contrast agent in a voxel measured over time.

"BOLD" or "BOLD imaging" herein refers to blood oxygen level dependent imaging, a method of detecting in vivo changes in blood oxygenation using functional magnetic resonance imaging.

"CBF" herein refers to cerebral blood flow, which is a measure of the blood supply to a particular voxel of the brain in a given time period.

"rCBF" herein refers to relative cerebral blood flow, which is the CBF for a particular voxel of the brain, relative to a reference voxel.

"CBV" herein refers to cerebral blood volume, which is the volume of blood contained in a particular voxel of the brain.

"rCBV" herein refers to relative cerebral blood volume, which is CBV for a particular voxel of the brain, relative to a reference voxel.

"CP" herein refers to choroid plexus, an organ in the ventricles of the brain that produces CSF.

"CSF" herein refers to cerebral spinal fluid, which is a bodily fluid that bathes the central nervous system, providing mechanical and immunological protection thereto.

"dOHb" herein refers to deoxyhemoglobin. dOHb is the deoxygenated form of hemoglobin, the oxygen carrying protein found in red blood cells. Since dOHb is paramagnetic, it can be detected with magnetic resonance imaging.

"[dOHb]" herein refers to a concentration of deoxyhemoglobin in the blood.

"Gd" herein refers to gadolinium, a paramagnetic element used in magnetic resonance imaging as a contrast agent.

"GBCA" herein refers to a gadolinium-based contrast agent. Examples of a GBCA include gadobutrol, gadodiamide, gadoteridol, gadoteric acid, gadoversetamide, gadoxetic acid, and gadopentetic acid.

"GM" herein refers to gray matter.

"MCA" herein refers to the middle cerebral artery.

"MTT" herein refers to mean transit time, which is the average period of time that blood spends within a particular voxel of the brain.

"$P_aO_2$" herein refers to partial pressure of oxygen in arterial blood.

"$P_aCO_2$" herein refers to partial pressure of carbon dioxide in arterial blood.

"$P_{ET}O_2$" herein refers to partial pressure of oxygen in end tidal (i.e., end expired) breath.

"$P_{ET}CO_2$" herein refers to partial pressure of carbon dioxide in end tidal (i.e., end expired) breath.

"MRI" herein refers to magnetic resonance imaging.

"$S_aO_2$" herein refers to arterial hemoglobin saturation.

"TE" herein refers to echo time.

"TR" herein refers to time of repetition.

"WM" herein refers to white matter.

The present disclosure provides an improved method of determining perfusion metrics by imposing a pre-determined arterial input function in a subject. Instead of observing a contrast signal and approximating the arterial input function based on a magnetic signal, the present disclosure provides a method of applying a pre-determined arterial input function with a known shape. Using a sequential gas delivery (SGD) device such as the RespirAct™ (Thornhill Medical: Toronto, Canada), it is possible to induce a stepwise decrease in deoxyhemoglobin. Since the concentration of deoxyhemoglobin is known and controlled, there is no requirement to measure the arterial input function.

The arterial input function can be induced by implementing a stepwise change in deoxyhemoglobin in the subject 330. FIG. 1 is a graph 100 displaying time on the x-axis and the subject's $P_{ET}O_2$ on the y-axis. As indicated at 202, a first $P_{ET}O_2$ is targeted in the subject 330 using sequential gas delivery, then a second $P_{ET}O_2$ that is higher than the first $P_{ET}O_2$ (indicated at 104) is targeted. With sequential gas delivery, $P_{ET}O_2$ is proportional to $P_aO_2$, so the concentration of contrast agent also increases in a stepwise fashion. The time required to re-oxygenate the arterial blood (indicated at 103) is negligible and therefore the contrast signal can be described with a square wave input function. The square wave input function may be used as the AIF in order to calculate a perfusion metric with greater certainty.

Figure 2:
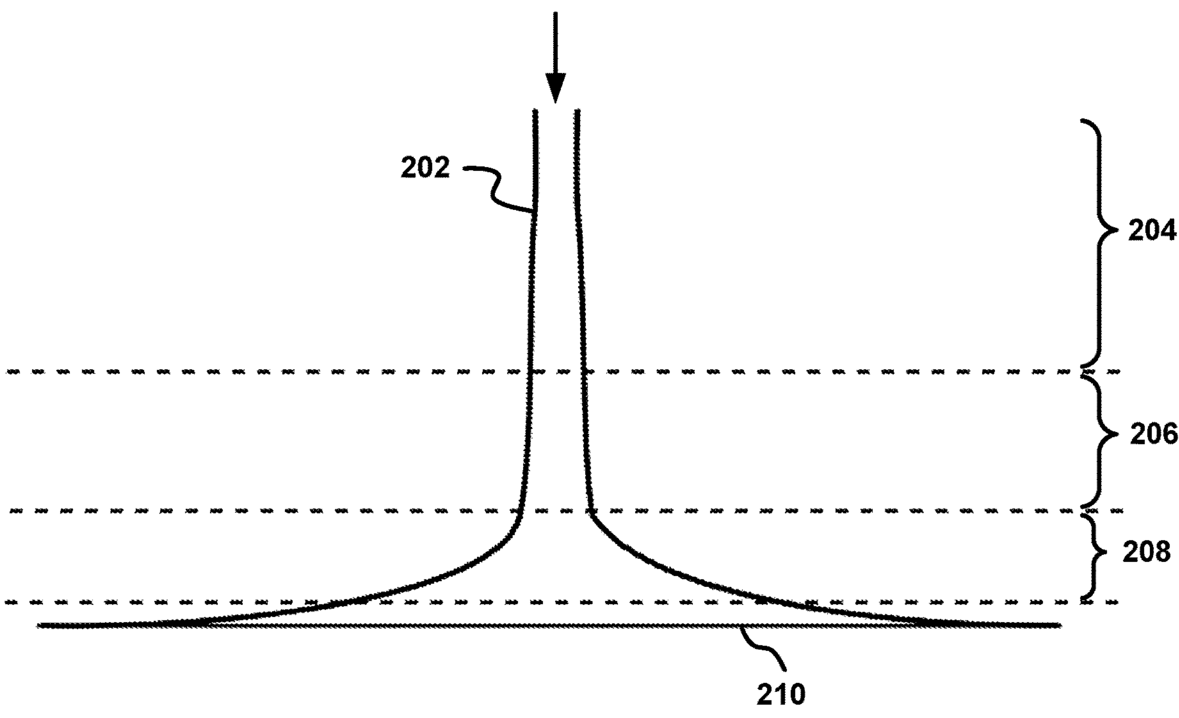
FIG. 2 is a graph of a step change in the concentration of deoxyhemoglobin in the lung.

This technique exploits the natural anatomy of the lung. Each bronchus in the lung branches into successively smaller and smaller passages before terminating at the alveoli. With each branch in the organ, the surface area available for respiration increases. FIG. 2 is a diagram representing the surface area of the lung 202 at successive branch orders. The width of the lung 202 represents the surface area and the height represents the number of branches starting from the bronchi at the top of the diagram. In the lower conducting airways (also known as central airways) 204, the surface area is small and branching minimally impacts the surface area. In the lower conducting airways (also known as peripheral airways) 206, the surface area remains small. The lower conducting airways 206 include 12$^{th}$ order branches which have a combined surface area of about 28 $cm^2$. In the acinar airways 208, the surface area begins to increase. The acinar airways 208 include $19^{th}$ order branches which have a combined surface area of about 0.1 $m^2$. In the alveoli 210, the surface area explodes to about 130 $m^2$. Thanks to this physiology, a volume of gas delivered to the lungs will equilibrize with the pulmonary capillaries in a very short amount of time.

Figure 3:
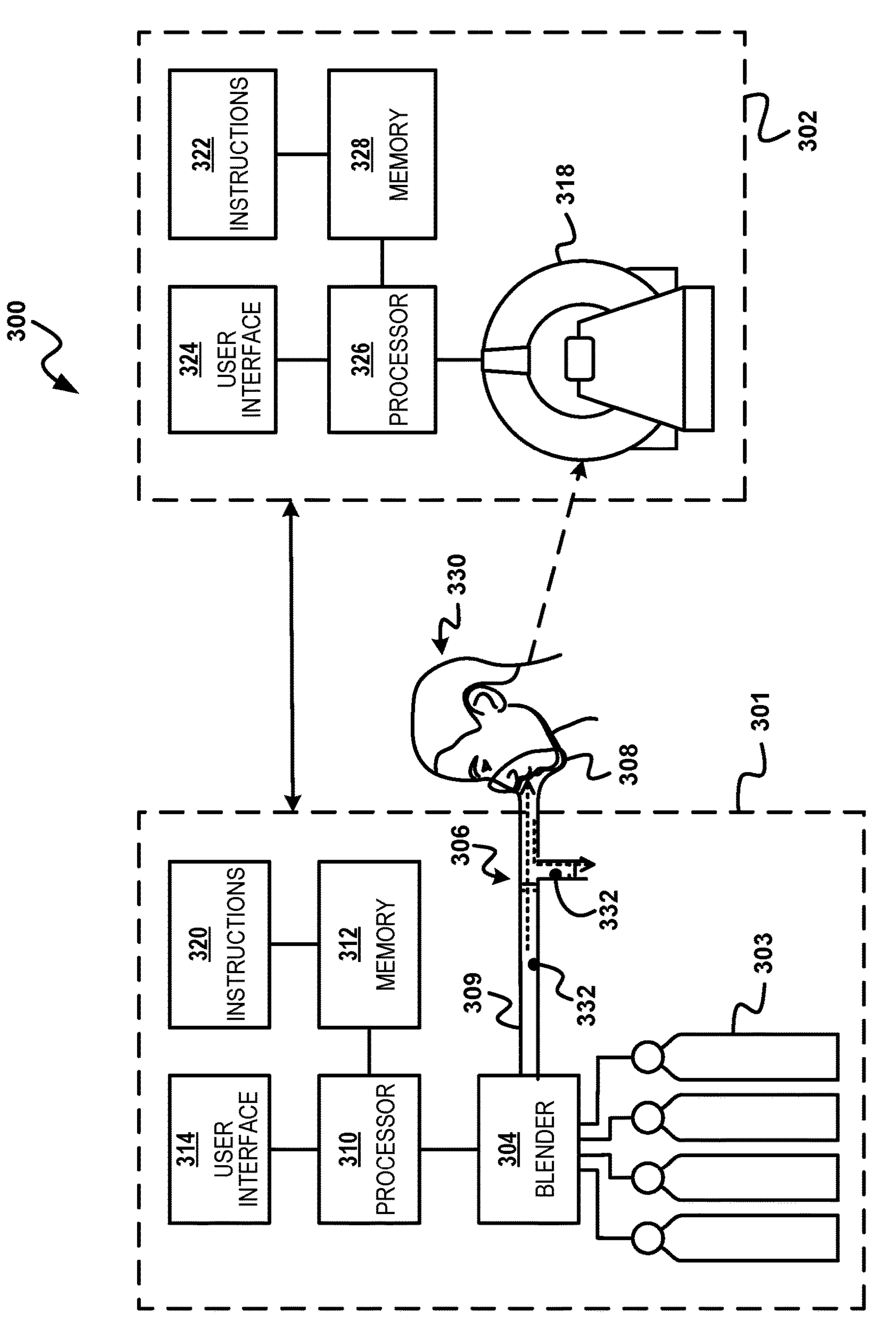
FIG. 3 is a block diagram of a system for determining a perfusion metric.

FIG. 3 shows a system 300 for determining a perfusion metric using deoxyhemoglobin as a contrast agent. The system 300 comprises a magnetic resonance imaging (MRI) system 302. The system 300 may further include a sequential gas delivery (SGD) device 301 to provide sequential gas delivery to a subject 330. The SGD device 301 may control an end tidal pressure of oxygen ($P_{ET}O_2$) while controlling an end tidal pressure of carbon dioxide ($P_{ET}CO_2$). In some examples, the SGD device 301 maintains $P_{ET}CO_2$ at normocapnia while varying the $P_{ET}O_2$. The SGD device 301 includes gas supplies 303, a gas blender 304, a mask 108, a processor 310, memory 312, and a user interface 314. The SGD device 301 may be configured to control $P_{ET}CO_2$ and $P_{ET}O_2$ by generating predictions of gas flows to actuate target end-tidal values. While $P_{ET}O_2$ is not necessarily equal to $P_aO_2$ when breathing room air, the SGD device 301 controls the delivery of gases in the lung such that $P_{ET}O_2$ approximates $P_aO_2$. The SGD device 301 may be a RespirAct™ device, made by Thornhill Medical™ of Toronto, Canada, specifically configured to implement the techniques discussed herein. For further information regarding sequential gas delivery, U.S. Pat. No. 8,844,528, US Publication No. 2018/0043117, and U.S. Pat. No. 10,850,052, which are incorporated herein by reference, may be consulted.

The gas supplies 303 may provide carbon dioxide, oxygen, nitrogen, and air, for example, at controllable rates, as defined by the processor 310. A non-limiting example of the gas mixtures provided in the gas supplies 303 is:

a. Gas A: 10% 02, 90% $N_2$;
b. Gas B: 10% 02, 90% $CO_2$;
c. Gas C: 100% $O_2$; and
d. Calibration gas: 10% $O_2$, 9% $CO_2$, 81% $N_2$.

The gas blender 304 is connected to the gas supplies 303, receives gases from the gas supplies 303, and blends received gases as controlled by the processor 310 to obtain a gas mixture, such as a first gas (G1) and a second gas (G2) for sequential gas delivery.

The second gas (G2) is a neutral gas in the sense that it has about the same $PCO_2$ as the gas exhaled by the subject 330, which includes about 4% to 5% carbon dioxide. In some examples, the second gas (G2) may include gas actually exhaled by the subject 330. The first gas (G1) has a composition of oxygen that is equal to the target $P_{ET}O_2$ and preferably no significant amount of carbon dioxide. For example, the first gas (G1) may be air (which typically has about 0.04% carbon dioxide), may consist of 21% oxygen and 79% nitrogen, or may be a gas of similar composition, preferably without any appreciable $CO_2$.

The processor 310 may control the gas blender 304, such as by electronic valves, to deliver the gas mixture in a controlled manner.

The mask 108 is connected to the gas blender 304 and delivers gas to the subject 330. The mask 108 may be sealed to the subject's face to ensure that the subject only inhales gas provided by the gas blender 304 to the mask 108. In some examples, the mask is sealed to the subject's face with skin tape such as Tegaderm™ (3M, Saint Paul, Minnesota). A valve arrangement 306 may be provided to the SGD device 301 to limit the subject's inhalation to gas provided by the gas blender 304 and limit exhalation to the room. In the example shown, the valve arrangement 306 includes an inspiratory one-way valve from the gas blender 304 to the mask 108, a branch between the inspiratory one-way valve and the mask 108, and an expiratory one-way valve at the branch. Hence, the subject 330 inhales gas from the gas blender 304 and exhales gas to the room.

The gas supplies 303, gas blender 304, and mask 108 may be physically connectable by a conduit 309, such as tubing, to convey gas. One or more sensors 332 may be positioned at the gas blender 304, mask 108, and/or conduits 309 to sense gas flow rate, pressure, temperature, and/or similar properties and provide this information to the processor 310. Gas properties may be sensed at any suitable location, so as to measure the properties of gas inhaled and/or exhaled by the subject 330.

The processor 310 may include a central processing unit (CPU), a microcontroller, a microprocessor, a processing core, a field-programmable gate array (FPGA), an application-specific integrated circuit (ASIC), or a similar device capable of executing instructions. The processor may be connected to and cooperate with the memory 312 that stores instructions and data.

The memory 312 includes a non-transitory machine-readable medium, such as an electronic, magnetic, optical, or other physical storage device that encodes the instructions. The medium may include, for example, random access memory (RAM), read-only memory (ROM), electrically erasable programmable read-only memory (EEPROM), flash memory, a storage drive, an optical device, or similar.

The user interface 314 may include a display device, speaker, microphone, touchscreen, mouse, keyboard, buttons, the like, or a combination thereof to allow for operator input and/or output.

Instructions 320 may be provided to carry out the functionality and methods described herein. The instructions 320 may be directly executed, such as a binary file, and/or may include interpretable code, bytecode, source code, or similar instructions that may undergo additional processing to be executed. The instructions 320 may be stored in the memory 312.

The system 300 includes an MRI system 302 for detecting a contrast agent in the subject 330. A suitable MRI system may include an imaging device 318 such as a 3T MRI system (Signa HDxt™: GE Healthcare, Milwaukee). The MRI system 302 may further include a processor 326, memory 328, and a user interface 324. Any description of the processor 326 may apply to the processor 310 and vice versa. Likewise, any description of memory 328 may apply to memory 312 and vice versa. Similarly, any description of instructions 322 may apply to instructions 320 and vice versa. Also, any description of user interface 324 may apply to user interface 314, and vice versa. In some implementations, the MRI system 302 and the SGD device 301 share one or more of a memory, processer, user interface, and instructions, however, in the present disclosure, the MRI system 302 and the SGD device 301 will be described as having respective processors, user interfaces, memories, and instructions. The processor 310 of the SGD device 301 transmits data to the processor 326 of the MRI system 302. The system 300 may be configured to synchronize MRI imaging obtained by the imaging device 318 with measurements obtained by the sensor 332.

The processor 326 may retrieve operating instructions 322 from the memory or may receive operating instructions 322 from the user interface 324. The operating instructions 322 may include image acquisition parameters which the imaging device 318 is configured to implement to acquire images of the subject 330. The parameters may include an interleaved echo-planar acquisition consisting of a number of contiguous slices, a defined isotropic resolution, a diameter for the field of view, a repetition time, and an echo time. In one implementation, the number of contiguous slices is 27, the isotropic resolution is 3 mm, the field of view is 19.6 cm, the echo time is 30 ms, and the repetition time (TR) is 2000 ms, however a range of values will be apparent to a person of ordinary skill in the art. The operating instructions 322 may also include parameters for a high-resolution T1-weighted SPGR (Spoiled Gradient Recalled) sequence for co-registering BOLD images and localizing the arterial and venous components. The SPGR parameters may include a number of slices, a dimension for the partitions, an in-plane voxel size, a diameter for the field of view, an echo time, and a repetition time. In one implementation, the number of slices is 176 m, the partitions are 1 mm thick, the in-plane voxel size is 0.85 by 0.85 mm, the field of view is 22 cm, the echo time is 3.06 ms, and the repetition time (TR) is 7.88 ms.

The processor 326 may be configured to use image analysis software such as Matlab™ 2015a and AFNI (Cox, 1996) or other processes generally known in the art, to analyze images acquired by the imaging device 318. As part of the analysis, the processor 326 may be configured to perform slice time correction for alignment to the same temporal origin and volume spatial re-registration to correct for head motion during acquisition. The processor 326 may be further configured to perform standard polynomial detrending. In one implementation, the processor 326 is configured to detrend using AFNI software 3dDeconvolve™ to obtain detrended data.

Figure 4:
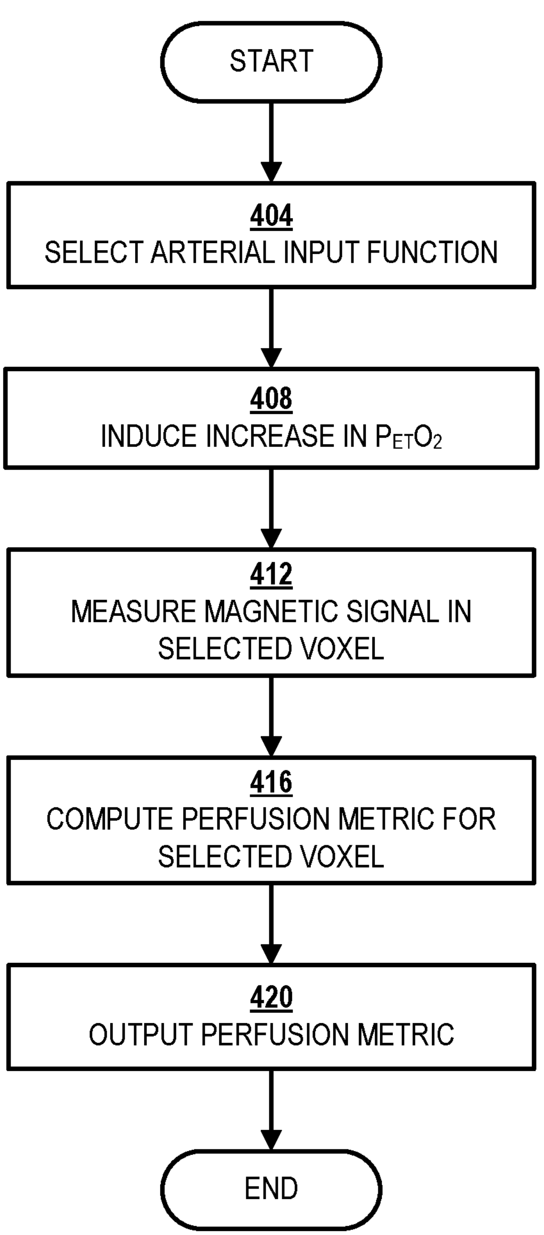
FIG. 4 is a flowchart of a method for determining a perfusion metric.

As shown in FIG. 4, the system 300 may be configured to measure a perfusion metric in the subject 330. FIG. 4 shows a method 400 of determining a perfusion metric by imposing an arterial input function and inducing a stepwise increase in arterial oxygenation. The system 300 may be controlled by instructions 320, 322.

At block 404, the processor 310 selects an arterial input function (AIF). The arterial input function describes the change in concentration of deoxyhemoglobin over time. The processor 310 may select the arterial input function based on the instructions 320 stored in memory 312 or based on instructions received at the user interface 314.

The arterial input function is a square input function and corresponds to a stepwise increase in $P_{ET}O_2$, as previously described with respect to FIG. 1. As part of block 404, the processor 310 selects a first $P_{ET}O_2$ and a second $P_{ET}O_2$ to target in the subject 330 using the SGD device 301. Since re-oxygenation can be achieved faster than de-oxygenation, the first $P_{ET}O_2$ is less than the second $P_{ET}O_2$. The difference between the first and second $P_{ET}O_2$ may be sufficient to induce a measurable decrease in the concentration of deoxyhemoglobin. In some examples, the first $P_{ET}O_2$ 202 induces hypoxia in the subject while the second $P_{ET}O_2$ 204 induces normoxia, however the method 400 is not particularly limited. In other examples, both the first and second $P_{ET}O_2$ are selected to induce varying levels of hypoxia. In yet other examples, both the first and second $P_{ET}O_2$ are selected to induce varying levels of normoxia. The quality of the signal may be affected if either the first or second $P_{ET}O_2$ induces hyperoxia, since hyperoxia can cause oxygen to dissolve in blood. In a specific example, the first $P_{ET}O_2$ is 40 mmHg and the second $P_{ET}O_2$ is 95 mmHg. Re-oxygenating the subject's blood from hypoxia to normoxia may be achieved within one breath, and in some examples less than one second, using a suitable SGD device.

As part of block 404, the processor 110 may convert the targeted $P_{ET}O_2$ values into $S_aO_2$ or [dOHb] values. The processor 110 may calculate the first and second $S_aO_2$ values based on the first and second $P_{ET}O_2$ values by applying the Hill equation, (shown below at Equation 1) or an equivalent method. In Equation 1, the dissociation constant (K) and the Hill coefficient (n) are determined using methods described in Balaban et al., 2013.

$$S_aO_2 = 100\frac{K(P_{ET}O_2)^n}{1+K(P_{ET}O_2)^n} \qquad \text{Equation 1}$$

Calculating the [dOHb] may further depend on the $P_{ET}CO_2$. Therefore, as part of block 404, the processor 110 may select the $P_{ET}CO_2$. In some examples, the $P_{ET}CO_2$ will be maintained as the $P_{ET}O_2$ varies. In particular examples, the $P_{ET}CO_2$ is selected to maintain normocapnia in the subject 330.

The processor 110 may further convert the first and second $P_{ET}O_2$ values into a square wave function. This square wave input function is designated to be the AIF and may be substituted for the AIF in subsequent perfusion calculations.

One example of a square input function is the Heaviside step function (Equation 2), however the square input function is not particularly limited.

$$H(x) := \begin{Bmatrix} 1, & x > 0 \\ 0, & x \le 0 \end{Bmatrix} \qquad \text{Equation 2}$$

Block 404 has been described above as first selecting the end tidal concentrations of gases and then computing the arterial input function based on the selected end tidal concentrations, however it will be understood that the reverse is also possible. The processor 310 may first determine the AIF and then calculate the end tidal concentrations of gases required to induce the selected AIF. In both implementations, the AIF may be pre-determined before the SGD device 301 induces a contrast signal in the subject 330. Consequently, perfusion metrics may be calculated without measuring a magnetic signal over a reference voxel.

At block 408, the SGD device 301 induces a single, stepwise increase in the subject's $P_aO_2$. The SGD device 301 may be controlled by instructions 320 stored in memory 312 or instructions received at the user interface 314. To induce a stepwise increase in concentration of $P_aO_2$, the SGD device 301 targets a first $P_{ET}O_2$ in the subject 330 and then targets a second $P_{ET}O_2$. While targeting the first and second $P_{ET}O_2$, the SGD device 301 may control the $P_{ET}CO_2$. In some examples, the SGD device 301 maintains the $P_{ET}CO_2$ while targeting the first and second $P_{ET}O_2$. In particular examples, the SGD device 301 maintains normocapnia while targeting the first and second $P_{ET}O_2$.

Rather than using a feedback loop to target the respective $P_{ET}O_2$ or $P_{ET}CO_2$ values, the SGD device 301 may be programmed to prospectively target an end-tidal concentration of gas. The approach of prospective targeting is to pre-calculate and administer an amount of nitrogen and oxygen for each successive breath to efficiently attain and maintain the targeted $P_{ET}O_2$ or $P_{ET}CO_2$, taking into account the lung volume, oxygen consumption, and breath size. The SGD device 301 may be programmed to automatically synchronize with the subject's breathing pattern. Methods for prospectively targeting end-tidal gas concentrations have been disclosed in Slessarev, M. et al. ("Prospective targeting and control of end-tidal CO2 and O2 concentrations." *J Physiol* 581, 3207-1219 (2007)) and Ito, S. et al. ("Non-invasive prospective targeting of arterial PCO2 in subjects at rest." *J Physiol* 586, 3675-3682 (2008)), which are incorporated by reference herein.

At block 412, the MRI system 302 measures the magnetic signals in a selected region of the subject's body. The MRI system 302 may be controlled by instructions 330 stored in memory or instructions received at the user interface 324. Herein, the region of interest will be described as a voxel. The voxel may be selected according to an input received at the user interface 324. The MRI system 302 measures the magnetic signal while the SGD device 301 controls the $P_{ET}O_2$ in the subject, and therefore the magnetic signal is responsive to the increase in $P_{ET}O_2$. Furthermore, the MRI system 302 may measure the magnetic signal in a plurality of selected voxels in the subject 330. In some examples, the plurality of voxels cover the entirety of an organ such as the brain, kidney, or thyroid gland.

In order to determine the effect of the contrast signal on the selected voxel, the MRI system 302 measures at least a first magnetic signal corresponding with the first $P_{ET}O_2$ and a second magnetic signal corresponding with the second $P_{ET}O_2$. In some examples, the MRI system 302 measures the magnetic signal repeatedly. The BOLD signal may need to be adjusted temporally to align with the arterial input function. The magnetic signals recorded at block 412 may be stored in memory 328 in association with the time at which the magnetic signals were recorded.

At block 416, the processor 326 computes a perfusion metric for the selected voxel based on the magnetic signal measured at block 412 and the pre-determined arterial input function selected at block 404. The perfusion metric may include MTT, CBV, and CBF, and may be calculated according to methods known in the art.

At block 420, the perfusion metric is output at a display comprising the user interface 324. The perfusion metric may be indicated as text, imagery, sound, colour, or the like. In examples where magnetic signals were obtained for a plurality of voxels, the perfusion metrics may be displayed as a perfusion map that locates each metric to its corresponding voxel.

Based on the perfusion metric calculated at block 420, the processor 326 may be further configured to identify a cerebrovascular pathology such as small vessel disease, venous collagenases, chronic inflammation, or multiple subcortical infarcts. The system 300 may be configured to display the pathology at the user interface 324.

The present disclosure provides a number of improvements to dynamic susceptibility contrast.

Since the contrast agent is administered through the lung, dispersion minimally affects the signal on arrival at the voxel artery. From the lung, the re-oxygenated blood only needs to travel from the pulmonary veins to the left atrium and left ventricle before reaching the tissues for imaging. In comparison, an intravenous contrast agent must be injected into a vein and therefore is sequentially diluted and therefore dispersed by joining with collateral veins, being washed into and out of the right atrium, right ventricle, left atrium, left ventricle, before arriving at the tissues for imaging. Moreover, a bolus of intravenous contrast agent cannot be square in profile due to unknown dispersion effects, and its concentration therefore, cannot be determined.

By imposing a contrast signal with a pre-determined concentration and signal profile, perfusion metrics can be calculated with greater consistency and accuracy. Since the shape of the AIF is known, it does not need to be approximated with a sinusoidal curve and deconvolved to the step function. Moreover, when the contrast signal is implemented by reoxygenation, the concentration of deoxyhemoglobin is pre-determined and is not in doubt or require any sort of measurement. As well as reducing noise, the pre-determined concentrations enhance granularity because the resolution is not limited by the subject's breathing rate, but by the TR which can be made to 200 ms or less on most 3T and 7T scanners. If instead, the perfusion metrics were based on measured $P_{ET}O_2$ values, data could only be gathered approximately every 5 seconds, when the subject exhales. Since the TR for MRI machines is typically every 2 seconds or less, the breathing rate would be very limiting.

The many features and advantages of the disclosure are apparent from the detailed specification and, thus, it is intended by the appended claims to cover all such features and advantages of the disclosure that fall within the true spirit and scope of the disclosure. Further, since numerous modifications and changes will readily occur to those skilled in the art, it is not desired to limit the disclosure to the exact construction and operation illustrated and described, and accordingly all suitable modifications and equivalents may be resorted to, falling within the scope of the disclosure.

What is claimed is:

1. A method of determining a perfusion metric in a subject comprising:
- pre-determining an arterial input function comprising a square input function, the square input function corresponding to a first end tidal partial pressure of oxygen ($P_{ET}O_2$) and a second $P_{ET}O_2$;
- inducing an increase in arterial partial pressure of oxygen in a subject by:
  - targeting the first $P_{ET}O_2$ with a sequential gas delivery device;
  - targeting the second $P_{ET}O_2$ with the sequential gas delivery device; and
  - controlling an end tidal partial pressure of carbon dioxide ($P_{ET}CO_2$) with the sequential gas delivery device;
  - wherein the first $P_{ET}O_2$ is less than the second $P_{ET}O_2$;
- measuring a magnetic signal in a selected voxel in the subject responsive to the increase in arterial partial pressure of oxygen; and
- outputting a perfusion metric for the selected voxel at a display, the perfusion metric calculated based on the pre-determined arterial input function and the magnetic signal,
- wherein the square wave input function is substituted for the arterial input function in the perfusion calculation.

2. The method of claim 1 wherein the sequential gas delivery device is configured to induce the increase in arterial partial pressure of oxygen within one second.

3. The method of claim 2 wherein the first $P_{ET}O_2$ corresponds to hypoxia in the subject and the second $P_{ET}O_2$ corresponds to normoxia in the subject.

4. The method of claim 3 wherein the first $P_{ET}O_2$ is about 40 mmHg and the second $P_{ET}O_2$ is about 95 mmHg.

5. The method of claim 3 wherein controlling $P_{ET}CO_2$ comprises maintaining normocapnia while targeting the first and second $P_{ET}O_2$.

6. The method of claim 1 wherein the perfusion metric is selected from the group consisting of cerebral blood flow, mean transit time, and cerebral blood volume.

7. The method of claim 1 wherein the magnetic signal is measured using blood oxygen level dependent magnetic resonance imaging.

8. A system for determining a perfusion metric in a subject comprising:

a processor for pre-determining an arterial input function comprising a square input function, the square input function corresponding to a first end tidal partial pressure of oxygen ($P_{ET}O_2$), and a second $P_{ET}O_2$;

a sequential gas delivery device configured to induce an increase in arterial partial pressure of oxygen in a subject by:

targeting the first $P_{ET}O_2$;

targeting the second $P_{ET}O_2$, wherein the first $P_{ET}O_2$ is less than the second $P_{ET}O_2$; and controlling an end tidal partial pressure of carbon dioxide ($P_{ET}CO_2$);

an imaging device configured to measure a magnetic signal in a selected voxel in the subject responsive to the increase in arterial partial pressure of oxygen; and a display configured to output a perfusion metric calculated for the selected voxel, the perfusion metric calculated based on the pre-determined arterial input function and the magnetic signal, wherein the square wave input function is substituted for the arterial input function in the perfusion calculation.

9. The system of claim 8 wherein the sequential gas delivery device is configured to induce the increase in arterial partial pressure of oxygen within one second.

10. The system of claim 9 wherein the first $P_{ET}O_2$ is selected to induce hypoxia in the subject and the second $P_{ET}O_2$ is selected to induce normoxia in the subject.

11. The system of claim 10 wherein the first $P_{ET}O_2$ is about 40 mmHg and the second $P_{ET}O_2$ is about 95 mmHg.

12. The system of claim 10 wherein controlling the $P_{ET}CO_2$ comprises maintaining normocapnia while targeting the first and second $P_{ET}O_2$.

13. The system of claim 8 wherein the perfusion metric is selected from the group consisting of cerebral blood flow, mean transit time, and cerebral blood volume.

14. The system of claim 8 wherein the imaging device is configured to measure the magnetic signal using blood oxygen level dependent magnetic resonance imaging.

15. A non-transitory computer-readable medium comprising instructions for determining a perfusion metric in a subject, the instructions comprising:

pre-determining an arterial input function comprising a square input function, the square input function corresponding to a first end tidal partial pressure of oxygen ($P_{ET}O_2$), and a second $P_{ET}O_2$;

controlling a sequential gas delivery device to induce an increase in arterial partial pressure of oxygen in a subject by:

targeting the first $P_{ET}O_2$;

targeting the second $P_{ET}O_2$, wherein the first $P_{ET}O_2$ is less than the second $P_{ET}O_2$; and controlling an end tidal partial pressure of carbon dioxide ($P_{ET}CO_2$);

measuring a magnetic signal in a selected voxel in the subject responsive to the increase in arterial partial pressure of oxygen; and outputting a perfusion metric for the selected voxel at a display, the perfusion metric calculated based on the pre-determined arterial input function and the magnetic signal, wherein the square wave input function is substituted for the arterial input function in the perfusion calculation.

16. The non-transitory computer-readable medium of claim 15 further comprising instructions for controlling the sequential gas delivery device to induce the increase in arterial partial pressure of oxygen within one second.

17. The non-transitory computer-readable medium of claim 15 wherein the first $P_{ET}O_2$ corresponds to hypoxia in the subject and the second $P_{ET}O_2$ corresponds to normoxia in the subject.

18. The non-transitory computer-readable medium of claim 17 wherein the first $P_{ET}O_2$ is about 40 mmHg and the second $P_{ET}O_2$ is about 95 mmHg.

19. The non-transitory computer-readable medium of claim 17 wherein controlling the $P_{ET}CO_2$ comprises maintaining normocapnia while targeting the first and second $P_{ET}O_2$.

20. The non-transitory computer-readable medium of claim 15 wherein the perfusion metric is selected from the group consisting of cerebral blood flow, mean transit time, and cerebral blood volume.

21. The non-transitory computer-readable medium of claim 15 wherein the magnetic signal is measured using blood oxygen level dependent magnetic resonance imaging.

* * * * *